United States Patent [19]

Lo et al.

[11] Patent Number: 5,439,454
[45] Date of Patent: Aug. 8, 1995

[54] COEXTRUDED MEDICAL GRADE PORT TUBING

[75] Inventors: Ying-Cheng Lo, Green Oaks; Indrajit T. Patel, Algonquin; Lecon Woo, Libertyville, all of Ill.; W. Wilson Cheung, Belchertown, Mass.; Michael T. K. Ling, Vernon Hills, Ill.

[73] Assignee: Baxter International Inc., Deerfield, Ill.

[21] Appl. No.: 883,001

[22] Filed: May 14, 1992

[51] Int. Cl.⁶ .................. A61M 5/00; F16L 11/00; B32B 1/08
[52] U.S. Cl. ...................... 604/264; 604/280; 428/36.91; 138/137
[58] Field of Search .............. 428/36.91; 604/264, 604/280; 138/137

[56] References Cited

U.S. PATENT DOCUMENTS

| | | |
|---|---|---|
| 3,561,493 | 2/1971 | Maillard .................... 428/36.91 X |
| 3,995,084 | 11/1976 | Berger et al. . |
| 4,087,587 | 5/1978 | Shida et al. . |
| 4,087,588 | 5/1978 | Shida et al. . |
| 4,233,367 | 11/1980 | Ticknor et al. . |
| 4,322,465 | 3/1982 | Webster . |
| 4,327,726 | 5/1982 | Kwong et al. . |
| 4,407,888 | 10/1983 | Crofts . |
| 4,417,753 | 11/1983 | Bacehowski et al. . |
| 4,479,989 | 10/1984 | Mahal . |
| 4,521,437 | 6/1985 | Storms . |
| 4,562,118 | 12/1985 | Maruhashi et al. . |
| 4,627,844 | 12/1986 | Schmitt ..................... 604/264 |
| 4,643,926 | 2/1987 | Mueller . |
| 4,707,389 | 11/1987 | Ward . |
| 4,724,028 | 2/1988 | Zabielski et al. . |
| 4,734,327 | 3/1988 | Vicik . |
| 4,735,855 | 4/1988 | Wofford et al. . |
| 4,753,222 | 6/1988 | Morishita . |
| 4,764,404 | 8/1988 | Genske et al. . |
| 4,767,651 | 8/1988 | Starczewski et al. . |
| 4,772,497 | 9/1988 | Maasola . |
| 4,778,697 | 10/1988 | Genske et al. . |
| 4,803,102 | 2/1989 | Raniere et al. . |
| 4,834,755 | 5/1989 | Silvestrini et al. . |
| 4,837,047 | 6/1989 | Sato et al. .................. 604/408 X |
| 4,915,893 | 4/1990 | Gogolewski et al. . |
| 4,923,470 | 5/1990 | Dumican . |
| 4,948,643 | 8/1990 | Mueller ...................... 428/36.6 |
| 4,996,054 | 2/1991 | Pietsch et al. . |
| 5,085,649 | 2/1992 | Flynn .......................... 604/282 |
| 5,096,775 | 3/1992 | Sato et al. ................... 428/327 |

FOREIGN PATENT DOCUMENTS

| | | |
|---|---|---|
| 0310143 | 7/1985 | European Pat. Off. . |
| 0216639 | 9/1985 | European Pat. Off. . |
| 0203630 | 4/1986 | European Pat. Off. . |
| 0380270 | 1/1990 | European Pat. Off. . |
| 0564231 | 3/1993 | European Pat. Off. . |

*Primary Examiner*—David H. Willse
*Attorney, Agent, or Firm*—Thomas S. Borecki; Charles R. Mattenson; Robert M. Barrett

[57] ABSTRACT

The present invention provides an improved coextruded medical port tubing. The medical port tubing provides characteristics that are desirable in the medical industry and therefore can be used as a medical port tubing in, for example, renal therapy or blood donor tubes. To this end, the present invention provides a coextruded medical grade port tubing comprising: an outer layer comprising a blend of polypropylene copolymer and styrene-ethylene-butylene-styrene copolymer; a tie layer; and a core layer comprising polyvinyl chloride.

18 Claims, 1 Drawing Sheet

COEXTRUDED MEDICAL GRADE PORT TUBING

BACKGROUND OF THE INVENTION

The present invention relates generally to materials for making medical grade products. More specifically, the present invention relates to medical grade port tubing.

It is known in the medical industry to house products such as fluids that are administered to a patient in plastic containers.

It is also known to use medical tubing, ports, to provide access either to a container or from a container. Such port tubing serves other purposes besides accessing the container, for example, as a conduit to a patient from a fluid source. Such medical port tubing has uses in such therapies as renal and blood.

Examples of therapies wherein flexible containers including port tubing are used include intravenous therapy, continuous ambulatory dialysis (CAPD), and blood therapy. In CAPD, the container includes a dialysis fluid that can be infused into the peritoneal of the patient through a tube, port, fused to the container.

Typically, for medical uses, there are a variety of characteristics that a medical port tube should have. Among the characteristics the port tube should exhibit is the ability to be RF (radio frequency) sealed to a material from which the container may be constructed. This allows the port tubing to be compatible with equipment used in certain of the medical industries. It is also desirable that the port tubing can be solvent bondable. For example, it is known in manufacturing containers with a port tubing to bond such tubings to a port closure (for example, PVC) using cyclohexanone to protect the sterility of the port tubing.

Furthermore, such port tubing should be sufficiently flexible as well as translucent. Additionally, the port tubing, if it is coextruded, must not easily delaminate.

Although most medical containers have been constructed from PVC, recently, much attention has been focussed on constructing non-PVC containers. Such port tubing, if it is to be used with a non-PVC container, must be compatible therewith.

SUMMARY OF THE INVENTION

The present invention provides an improved coextruded medical port tubing and materials for making same. The medical port tubing provides characteristics that are desirable in the medical industry and therefore can be used as a medical port tubing in, for example, renal therapy or blood donor tubes. Furthermore, the port tubing can be used with a non-PVC container.

To this end, the present invention provides a coextruded medical grade port tubing comprising: an outer layer comprising a blend of polypropylene copolymer and styrene-ethylene-butylene-styrene copolymer; a tie layer; and a core layer comprising polyvinyl chloride.

In an embodiment, the tie layer comprises a blend of polyester, polypropylene copolymer, styrene-ethylene-butylene-styrene copolymer, and ethylene vinyl acetate. Preferably, the tie layer is a blend comprising: approximately 30 to about 60% by weight copolyester; approximately 0 to about 20% by weight polypropylene copolymer; approximately 30 to about 60% by weight styrene-ethylene-butylene-styrene copolymer; and approximately 0 to about 30% by weight ethylene vinyl acetate.

In an embodiment, the outer layer of the port tube comprises approximately 40 to about 99% by weight polypropylene copolymer and approximately 1 to about 60% by weight styrene-ethylene-butylene-styrene copolymer.

In an embodiment, the present invention provides a coextruded medical grade port tubing comprising: an outer layer comprising a blend of polypropylene copolymer and styrene-ethylene-butylene-styrene copolymer; a tie layer comprising a blend of polyester, polypropylene copolymer, styrene-ethylene-butylene-styrenecopolymer, and ethylene vinyl acetate; and a core layer of polyvinyl chloride. This structure allows the outer layer to be bonded to polyolefin surface layer film and allows the inner layer to be solvent bonded to PVC material.

In an embodiment, the layers of the port tubing have the following thickness ratios: outer layer approximately 2.5 to about 30%; tie layer approximately 2.5 to about 20%; and core layer approximately 50 to about 95%. Preferably, the outer and tie layer are thin enough to allow rapid and sufficient heat transfer from the PVC heat generation layer to the outer layer for welding.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a coextruded medical grade port tubing and material for making same that achieves many of the characteristics that are desirable, in the medical industry, for such port tubing. For example, the port tubing, in an embodiment, exhibits RF sealability, ability to solvent bond, flexibility, translucence, and ability to not delaminate after severe bending or autoclaving.

Figure 1:
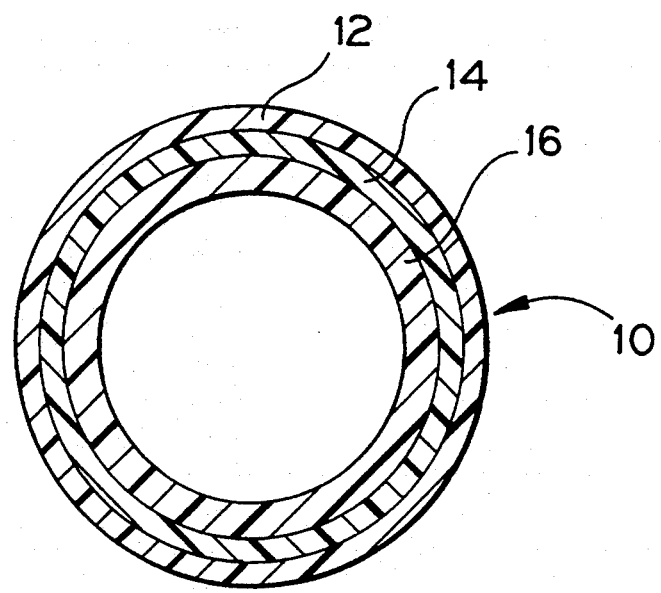
FIG. 1 illustrates a cross-sectional view of a coextruded port tube constructed pursuant to an embodiment of the present invention.

Referring to FIG. 1, the present invention provides a coextruded medical grade port tubing 10 comprising: an outer layer 12 comprising a blend of polypropylene copolymer and styrene-ethylene-butylene-styrene copolymer; a tie layer 14 comprising preferably a blend of polyester, polypropylene copolymer, styrene-ethylene-butylene-styrene copolymer, and ethylene vinyl acetate; and a core layer 16 of polyvinyl chloride.

The medical grade port tubing 10 is autoclavable and can be RF sealable to a non-PVC container having a polyolefin blend or polyolefin surfaces. Additionally, the composition can be solvent bonded to a PVC closure using cyclohexanone, MEK (methyl ethyl ketone) or other solvent. In this regard, the outer layer 12 is able to bond to a polyolefin surface layer film while the core layer 16 can be bonded to a PVC material.

Preferably, the tie layer 14 is a blend of material comprising: approximately 30 to 60% copolyester by weight, for example, Hytrel available from DuPont; approximately 0 to 20% by weight polypropylene copolymer (approximately 2-6% by weight polyethylene); approximately 30 to about 60% by weight styrene-ethylene-butylene-styrene copolymer, for example, Kraton; and approximately 0 to about 30% by weight ethylene vinyl acetate.

Preferably, the outer layer 12 comprises approximately 40 to 99% by weight polypropylene copolymer that includes approximately 2 to 6% by weight polyethylene, and approximately 1 to 60% by weight styrene-ethylene-butylene-styrene copolymer, for example, Kraton.

The core layer 16 can comprise PVC plasticized with DEHP, or other material. Likewise, the core layer 16 can comprise non-plasticized PVC.

Preferably, the medical grade port tubing 10 has a structure so that it has the following ratio of layer thicknesses: the outer layer 12 comprises approximately 2.5% to about 30% of the total cross-sectional thickness of the port tube; the tie layer 14 comprises approximately 2.5% to 20% of the total cross-sectional thickness of the tube; and the core layer 16 of the structure comprises approximately 50% to 95% of the total cross-sectional thickness of the structure. By providing thin outer and tie layers 12 and 14, the port tubing 10 can be R.F. sealed to a plastic film.

The resultant medical grade port tubing 10 is flexible and translucent. Accordingly, when used as a medical tubing, one can see air bubbles or needles, for example, through the port tubing. Additionally, the port tubing 10 does not easily delaminate even after severe bending either before or after autoclaving.

Figure 2:
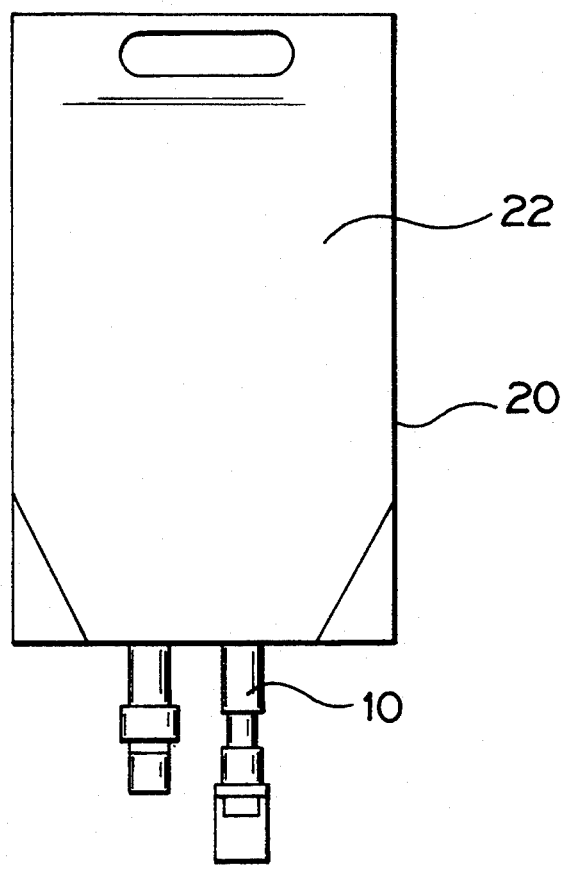
FIG. 2 illustrates a perspective view of a container including the port tubing of the present invention.

The port tubing 10 of FIG. 1 can be used with a medical container 20 illustrated in FIG. 2. In a preferred embodiment, the container 20 is constructed from a non-PVC material. In a preferred embodiment, the container is constructed from a four layer film comprising: polypropylene copolymer,Kraton ®/ethylene vinyl acetate/acid modified ethylene vinyl acetate/PCCE.

The port tubing 10 provides access to and away from an interior 22 of the container 20. The port tubing 10 of the present invention is believed to be particularly suitable for use in renal applications, especially CAPD. However, the port tubing 10 can be used to construct other medical products.

By way of example, and not limitation, examples of the present invention will now be given.

EXAMPLE NO. 1

Coextruded port tubings were constructed and evaluated as follows.

The following materials were used:
Core layer: DEHP Plasticized PVC;
Tie layer:
  50 weight % Kraton G-1660 (Shell);
  38 weight % Hytrel 4056 (DuPont);
  10 weight % UE 697000 (Quantum); and
  2 weight % Polypropylene copolymer 23M2 (El Paso);
Outer layer: 60 weight % Polypropylene copolymer- Fina 8473 (Fina); and
40 weight % Styrene-ethylene-butylene-styrene- Kraton G-1652 (Shell).

The following processing conditions were used:

| • Nominal Setting | | | |
|---|---|---|---|
| Core Layer 1¼" Davis Standard | | Tie Layer 1: Davis Standard | |
| Barrel Zone # | Set | Barrel Zone # | Set |
| 1) | 325° F. | 1) | 450° F. |
| 2) | 325° F. | 2) | 450° F. |
| 3) | 325° F. | 3) | 450° F. |
| 4) | 325° F. | | |
| Die Zone # | Set | Die Zone # | Set |
| 1) | 325° F. | 1) | 450° F. |
| Adapter | 325° F. | | |
| Screw R.P.M.: 60 | AMPS: 12 | Screw R.P.M.: 21 | AMPS: 4 |
| Screw Type: | Pin | Screw Type | Maddox |
| Screw Pack: | 40-60-40 | Screw Pack: | 40-60-40 |
| Head Pressure: | 5800 P.S.I. | Head Pressure | 180 P.S.I. |

| Outer Layer 1" Davis-Standard | | | |
|---|---|---|---|
| Barrel Zone # | Set | (Tri Die Set-Up) | |
| 1) | 400° F. | Die Pin O.D.: | .300" O.D. |
| 2) | 400° F. | Die Bushing: | .375" I.D. |
| 3) | 400° F. | | |
| Die Zone # | Set | (Vacuum Tank Set-Up) | |
| 1) | 400° F. | Sizer I.D.: | .390" |
| | | Water Temp.: | 53.8" |
| | | Vacuum: | Pot. Setting 25.5 |
| | | Die to Tank: | 1" |
| Screw R.P.M.: 18 | AMPS: 4 | Pull or Setting: | 33 f.P.M. |
| Screw Type: | Barrier | | |
| Screw Pack: | 40-60-40 | | |
| Head Pressure: | N/A | | |

The resultant port tubing included a core layer having a thickness of 0.71 mm, a tie layer of 0.05 mm, and an outer layer of 0.05 mm.

The port tubing was autoclaved. The port tubing characteristics were then evaluated, after autoclaving, and are set forth below in the table. The bonding force between the outer and tie layer was found to be strong. An initial separation between the outer and tie layer could not be initiated. The bonding force between the tie and core layer was 1.1 to 1.2 lbs ./0.5 inches.

PORT TUBING MATERIAL EVALUATION

| | Tubing Characteristics | | | Post Autoclaving | | |
|---|---|---|---|---|---|---|
| Tubing Materials | Processing | Bond* | Texture | Bond* | Texture | COMMENTS |
| Example #1 | Good | 9 | Smooth | 9 | Smooth | Very difficult to peel |

1. Assume bonding strength of PVC to PVC by cyclohexanone is 10. Data results are subjective due to manual testing. (*)

Example No. 1 demonstrates that the port tubing of the present invention meets the necessary requirements of a port tubing. Indeed, the port tubing exhibits characteristics that are better than current PVC port tubing since a typical PVC port will not bond to a non-PVC container.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A coextruded medical grade port tubing comprising:
   an outer layer, having a thickness comprising approximately 2.5 to about 30% of the total cross-sectional thickness of the tubing, and comprising a blend of polypropylene copolymer and styrene-ethylene-butylene-styrene copolymer;
   a tie layer, having a thickness comprising approximately 2.5 to about 20% of the total cross-sectional thickness of the port tubing; and
   a core layer of polyvinyl chloride, having a thickness comprising approximately 50 to about 95% of the total cross-sectional thickness.

2. The coextruded medical grade port tubing of claim 1 wherein the tie layer comprises a blend of polyester, polypropylene copolymer, styrene-ethylene-butylene-styrene copolymer, and ethylene vinyl acetate.

3. The coextruded medical grade port tubing of claim 1 wherein the tie layer is a blend comprising:
   approximately 30 to about 60% by weight copolyester;
   approximately 0 to about 20% by weight polypropylene copolymer;
   approximately 30 to about 60% by weight styrene-ethylene-butylene-styrene copolymer; and
   approximately 0 to about 30% by weight ethylene vinyl acetate.

4. The medical grade port tubing of claim 3 wherein the polypropylene copolymer of the tie layer includes approximately 2 to about 6% by weight polyethylene.

5. The coextruded medical port tubing of claim 1 wherein the outer layer comprises:
   approximately 40 to about 99% by weight polypropylene copolymer; and
   approximately 1 to about 60% by weight styrene-ethylene-butylene-styrene copolymer.

6. The coextruded medical port tubing of claim 1 wherein the outer layer comprises approximately 60% by weight polypropylene copolymer and approximately 40% by weight styrene-ethylene-butylene-styrene.

7. The coextruded medical grade port tubing of claim 1 wherein the polypropylene copolymer comprises approximately 2 to about 6% by weight polyethylene.

8. A coextruded medical grade port tubing that is sealable to an olefin film and solvent bondable to PVC comprising:
   an outer layer, having a thickness of approximately 2.5 to about 30% of the total cross-sectional thickness of the port tubing, comprising a blend of polypropylene copolymer and styrene-ethylene-butylene-styrene copolymer;
   a tie layer, having a thickness of approximately 2.5 to about 20% of the total cross-sectional thickness of the port tubing, comprising approximately 30 to about 60% by weight copolyester, approximately 0 to about 20% by weight polypropylene copolymer, approximately 30 to about 60% by weight styrene-ethylene-butylene-styrene copolymer, and approximately 0 to about 30% by weight ethylene vinyl acetate; and
   a core layer, having a thickness of approximately 50 to about 95% of the total cross-sectional thickness of the port tubing, comprising polyvinyl chloride.

9. The coextruded medical port tubing of claim 8 wherein the outer layer comprises:
   approximately 40 to about 99% by weight polypropylene copolymer; and
   approximately 1 to about 60% by weight styrene-ethylene-butylene-styrene copolymer.

10. The coextruded medical port tubing of claim 8 wherein the outer layer comprises approximately 60% by weight polypropylene copolymer and approximately 40% by weight styrene-ethylene-butylene-styrene.

11. The coextruded medical grade port tubing of claim 8 wherein the polyvinyl chloride includes a plasticizer.

12. The coextruded medical grade port tubing of claim 8 wherein the polyvinyl chloride does not include a plasticizer.

13. A non-PVC medical container for housing medical fluid including a coextruded medical grade port tubing comprising:
   an outer layer comprising a blend of polypropylene copolymer and styrene-ethylene-butylene-styrene copolymer and having a thickness of approximately 2.5 to about 30% of the total cross-sectional thickness of the port tubing;
   a tie layer, having a thickness of approximately 2.5 to about 20% of the total cross-sectional thickness of the port tubing; and
   a core layer, having a thickness of approximately 50 to about 95% of the total cross-sectional thickness of the port tubing, comprising a blend of polyvinyl chloride.

14. The medical container of claim 13 wherein the tie layer of the port tubing comprises a blend of polyester, polypropylene copolymer, styrene-ethylene-butylene-styrene copolymer, and ethylene vinyl acetate.

15. The medical container of claim 13 wherein the tie layer of the port tubing is a blend comprising:
   approximately 30 to about 60% by weight copolyester;
   approximately 0 to about 20% by weight polypropylene copolymer;
   approximately 30 to about 60% by weight styrene-ethylene-butylene-styrene copolymer; and
   approximately 0 to about 30% by weight ethylene vinyl acetate.

16. The medical container of claim 13 wherein the outer layer of the port tubing comprises:
   approximately 40 to about 99% by weight polypropylene copolymer; and
   approximately 1 to about 60% by weight styrene-ethylene-butylene-styrene copolymer.

17. The medical container of claim 13 wherein the polyvinyl chloride of the port tubing includes a plasticizer.

18. The medical container of claim 13 wherein the polyvinyl chloride of the port tubing does not include a plasticizer.

* * * * *